(12) United States Patent
Ullman et al.

(10) Patent No.: US 8,083,783 B2
(45) Date of Patent: Dec. 27, 2011

(54) SURGICAL FIXATION PIN

(75) Inventors: Michael Ullman, Onsala (SE); Carl Ekholm, Onsala (SE)

(73) Assignee: Swemac Innovation AB, Linköping (SE)

( * ) Notice: Subject to any disclaimer, the term of this patent is extended or adjusted under 35 U.S.C. 154(b) by 744 days.

(21) Appl. No.: 11/887,746

(22) PCT Filed: Apr. 10, 2006

(86) PCT No.: PCT/SE2006/000429
§ 371 (c)(1),
(2), (4) Date: Jan. 22, 2008

(87) PCT Pub. No.: WO2006/107264
PCT Pub. Date: Oct. 12, 2006

(65) Prior Publication Data
US 2008/0281363 A1    Nov. 13, 2008

(51) Int. Cl.
*A61B 17/04* (2006.01)
*A61B 17/84* (2006.01)
*A61B 17/86* (2006.01)
*A61F 2/08* (2006.01)

(52) U.S. Cl. .................................................. 606/329
(58) Field of Classification Search ............... 606/329, 606/67
See application file for complete search history.

(56) References Cited

U.S. PATENT DOCUMENTS

| | | | | |
|---|---|---|---|---|
| 4,298,299 A | * | 11/1981 | Quarles | 411/514 |
| 4,483,335 A | * | 11/1984 | Tornier | 606/64 |
| 4,915,092 A | * | 4/1990 | Firica et al. | 606/67 |
| 5,041,114 A | * | 8/1991 | Chapman et al. | 606/62 |
| 5,324,152 A | * | 6/1994 | Anderson, IV | 411/530 |
| 5,709,682 A | * | 1/1998 | Medoff | 606/60 |
| 5,941,878 A | * | 8/1999 | Medoff | 606/60 |
| 6,135,693 A | * | 10/2000 | Leitzke et al. | 411/530 |
| 6,248,109 B1 | * | 6/2001 | Stoffella | 606/75 |
| 6,358,250 B1 | | 3/2002 | Orbay | 606/69 |
| 6,364,882 B1 | | 4/2002 | Orbay | 606/69 |
| 6,379,359 B1 | * | 4/2002 | Dahners | 606/62 |
| 6,440,135 B2 | | 8/2002 | Orbay et al. | 606/69 |
| 6,579,293 B1 | | 6/2003 | Chandran | 606/64 |
| 6,767,351 B2 | | 7/2004 | Orbay et al. | 606/69 |
| 2005/0010228 A1 | * | 1/2005 | Medoff | 606/74 |

FOREIGN PATENT DOCUMENTS

| | | |
|---|---|---|
| EP | 0 693 272 A1 | 1/1996 |
| EP | 693272 A1 * | 1/1996 |
| FR | 2 728 155 A1 | 6/1996 |
| WO | WO 01/56452 A2 | 8/2001 |
| WO | WO 03/068080 A1 | 8/2003 |

* cited by examiner

*Primary Examiner* — Thomas C. Barrett
*Assistant Examiner* — David Bates
(74) *Attorney, Agent, or Firm* — Alfred J. Mangels (57) ABSTRACT

A surgical fixation pin for use in fractures of bones in arms or other body parts to achieve support of the bone while the fracture heals. The pin is formed of a spring material and includes at opposite ends an angled, rounded front section and a double bent, extracortical section equipped with a fixation eye for receiving a fixation screw for securing the pin to a bone at a fracture site.

10 Claims, 13 Drawing Sheets

SURGICAL FIXATION PIN

BACKGROUND OF THE INVENTION

1. Field of the Invention

The present invention relates to a pin for use in fractured bones in arms or other parts of the body, to bring about support of the fractured bone while it is healing.

2. Description of the Related Art

It is generally known within the health care field that in the treatment of fractured bones means are used to allow reinforcement and support to the area surrounding a fracture in the bone in question.

Fractures of the distal forearm (wrist fractures) are the most common of all fractures (annual incidence about 3,000/1,000,000 inhabitants in the industrialized world) and constitutes by it's abundance a major therapeutic problem. Simple fractures are treated with just a bandage while more complex fractures often require open reduction and plate fixation. For a large number of the intermediate complex fractures the choice of treatment is less obvious; while plate fixation may be a too extensive and expensive procedure bandage immobilization may be insufficient to hold fracture fragments in the desired position while the fracture heals. Other therapeutic modalities also have their drawbacks: classic external fixation immobilizes the wrist joint during treatment and wrist stiffness may ensue. To avoid that, the external fixation is often removed before the fracture is consolidated, which may lead to secondary displacement of the fracture.

Another method is to use straight fine wires (1.5-2.0 mm in diameter) drilled into the fragments or introduced through the fracture site. While that is a simple and minimally invasive procedure it requires power tools. Also, the wires, being left protruding through the skin, have to be removed before the patient is able to mobilize her wrist.

The second bone of the forearm, the ulna, is notoriously difficult to fix, and fractures of the distal ulna are therefore often neglected. Pins have been used, among others, to hold together the bone fragments, or they have been inserted in the bone's inner canal. The pin has then either been allowed to remain in place after the fractured bone has healed, or it has been extracted afterwards. Plates similar to angle iron have also been used and are attached with screws to the bone by the fracture. Examples of such aids are shown in International Publication No. WO 01/56452 A2.

It has been difficult to operate in such supports by the fracture area, and even more difficult to remove them. Neither have those supports constituted an especially good pin in themselves, i.e., they have not interacted with the bone to achieve contact against the same during simultaneous tensioning of the pin. The introduction of the pin in the bone has not been facilitated with similarly known pins, and neither has the screwing of them into the bone been proven to be easy to achieve.

It is difficult to insert pins in the bone, and sometimes a power drill is required. It is also difficult to securely anchor the pin in the bone, which is why they frequently slide out. In addition, they are frequently left protruding from the skin, with the risk of both inflammation around the pin as well as infection, which can spread to the bone and develop into osteomyelitis.

An object of the present invention is thus primarily to produce a pin that is suitable for use in the healing of fractured bones in the arms or other parts of the body, and which solves, among others, the problems identified above, and which is also easy and cost effective to manufacture.

SUMMARY OF THE INVENTION

The object is achieved by means of a pin in accordance with the present invention, which pin is essentially characterized in that on opposite ends of the pin, it includes an angled, rounded front section and one double bent extra cortical equipped with an anchor eye, and is formed of spring material.

Previously disclosed in published French application FR 2,728,155-A1 is a so-called intramedullary nail.

The present invention is intended for fixation of moderately complex fractures. The present implants are pins specifically designed for fixation of wrist fractures, but with modifications it can be extended to other fractures. The implant is made of 1.6 mm wire (but other materials or dimensions can be used) with mechanical properties suitable for this particular use. The larger part of the implant is introduced through the fracture line into the intramedullary canal of the main body of the fractured bone and thus becomes stabilized. The lesser part of the implant, anatomically shaped to lie flush against the outer cortex of the distal fragment, stabilizes the fracture by serving as a support. Since the implant is introduced through the fracture line and into the intramedullary canal no power tools are needed. The implant has a low profile and is anatomically shaped and therefore does not normally require removal—a second procedure is thereby avoided, and the fracture is supported during the consolidation period even while normal activity with the wrist and hand is resumed.

The form of the implants is as follows:

Implants for the Radius

The implants meant to fix fractures of the radius have the same basic configuration and functions; small variations in the design are made with respect to variations the anatomy of the specific site where they are used.

The intramedullary portion is straight but has a curved tip with a rounded end to facilitate its introduction into the intramedullary canal.

The extramedullary portion is shaped to follow the anatomy of the outer cortex of the radius. It is constituted of a double wire connected by a 180° distal bend made into the shape of a hoop. That design enlarges the supporting interface between implant and bone.

The extramedullary and intramedullary parts are roughly parallel but not coaxial—they are connected by an intermediate part at about a 90° angle to each of the other parts. The length of the intermediate part corresponds to the thickness of the cortical wall of the radius at the fracture site. The transverse part prevents the implant from sliding out of place.

One of the double wires is extended beyond the connecting part to form a fork with the intramedullary part. That is intended to stabilize the implant against the outer wall of the main fracture body.

The hoop formed at the distal end of the implant is shaped to fit a screw, which can optionally be used to stabilize the distal fragment.

Implants for the Ulna

The ulnar implant differs from the radial implant in the respect that it is intended to be fixed in position with one or two screws.

The intramedullary portion is straight and has a pointed tip to allow its introduction through the distal part of the ulna into the intramedullary canal;

The extramedullary portion has two hoops, the proximal one for screw fixation of the implant itself to the shaft of the ulna, the distal one for optional screw fixation of the distal fragment; and The distal fragment is fixed in position by being sandwiched between the intramedullary and extramedullary portions of the implant.

BRIEF DESCRIPTION OF THE DRAWINGS

The invention is described below in terms of a number of preferred embodiments, whereby reference is made to the appended drawings, in which.

DESCRIPTION OF THE PREFERRED EMBODIMENTS

Figure 1:
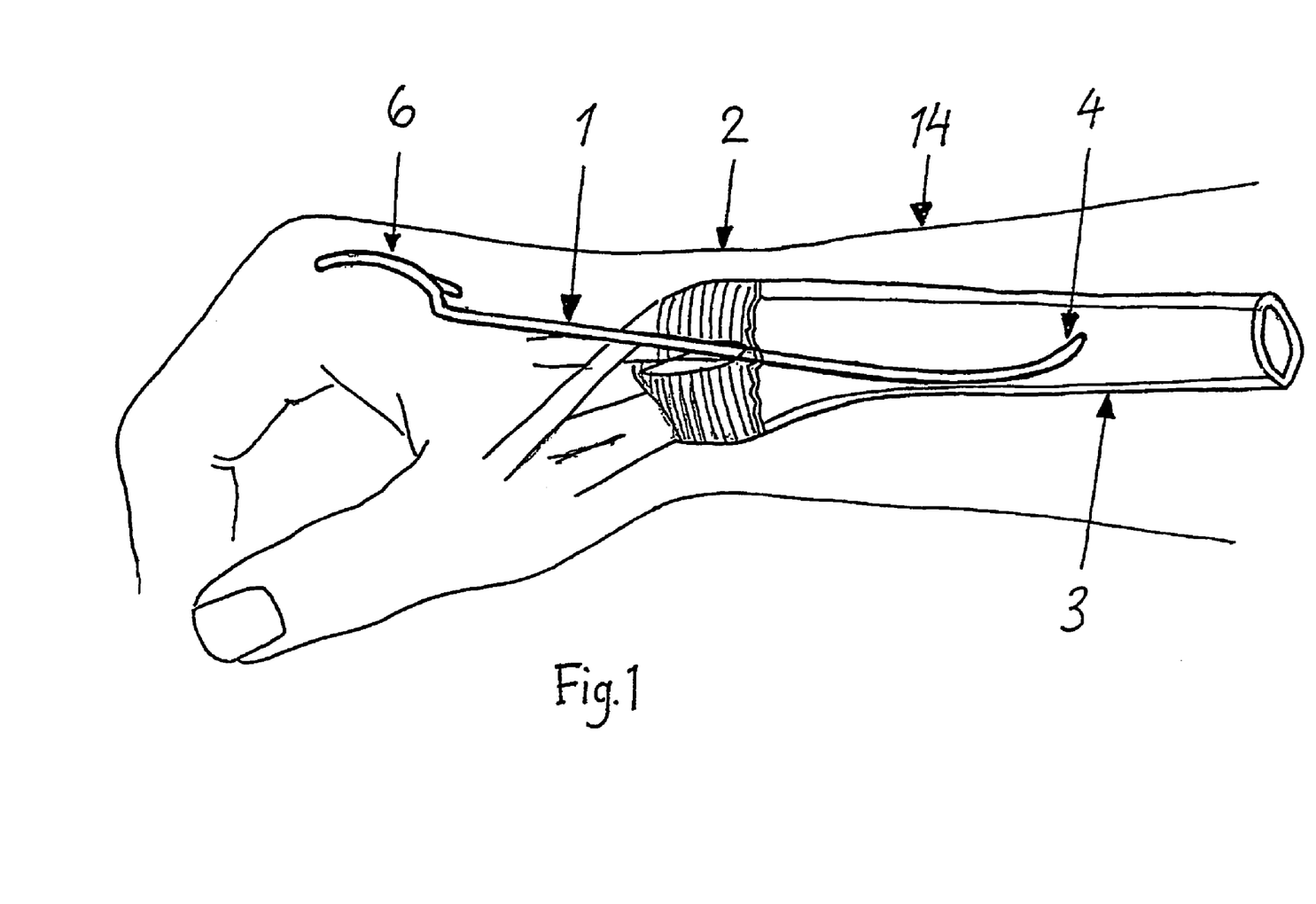
FIG. 1 schematically shows a pin in accordance with the present invention implanted in a forearm.

Referring to FIG. 1, a surgical fixation pin 1 in accordance with the present invention is included in a simple and effective system to be used as an aid when treating irregular distal radius and ulna fractures 2. The pin 1 is arranged to achieve maximum stability by using the smallest possible operation and implant. Pin 1 is further arranged to make it easy to insert through the fracture 2 and will be distinctive when inserted against the edge of the fracture in the proximal bone fragment in position in bone 3. A fixing device in the form of bone screw 9 (see FIG. 14) is ideal to be utilized together with a fixation pin of the type described herein to further achieve the stability of the fracture site. The insertion of the pin 1 is done through a small incision, as is shown in FIG. 1.

A pin 1 (FIGS. 1-4); 101 (FIGS. 5-10); 201 (FIG. 14) that is ideal for use with fracture 2 on bone 3 in arms 14 or other body parts, to achieve support and stability to the bone 3 when healing the fracture 2 in question, is formed in accordance with the present invention principally of three different designs. The different pins 1; 101; 201 are called "Radius Contour Pin," "Radius dorsal Pin," and "Ulna Pin," respectively.

In accordance with the invention, the characteristic for all of those pins is that at opposite ends 1A, 1B (see FIG. 2); 101A, 101B (see FIG. 5), and 201A and 201B (see FIG. 14) the pins have an angled, rounded front part 4; 104; and 204, respectively, and a double bend with anchor eye 5; 105; 205 at a rear support part 6; 106; 206, respectively. Pin sections 7A, 7B; 107A, 107B; 207A, 207B lie parallel and in close contact with each other. Each of pins 1; 101; 201 is formed of a spring material, preferably spring steel.

The rear support parts 6; 106; 206 of the pins are formed by a bend, from the center sections 1C; 101C; 201C, of the pins with respective blunt angle bent sections 8; 108; 208, and from each of the bent sections a respective extending end section, which is double bent with each pair of pin end sections 7A, 7B; 107A, 107B; 207A, 207B lying in tight contact with each other.

Figure 2:
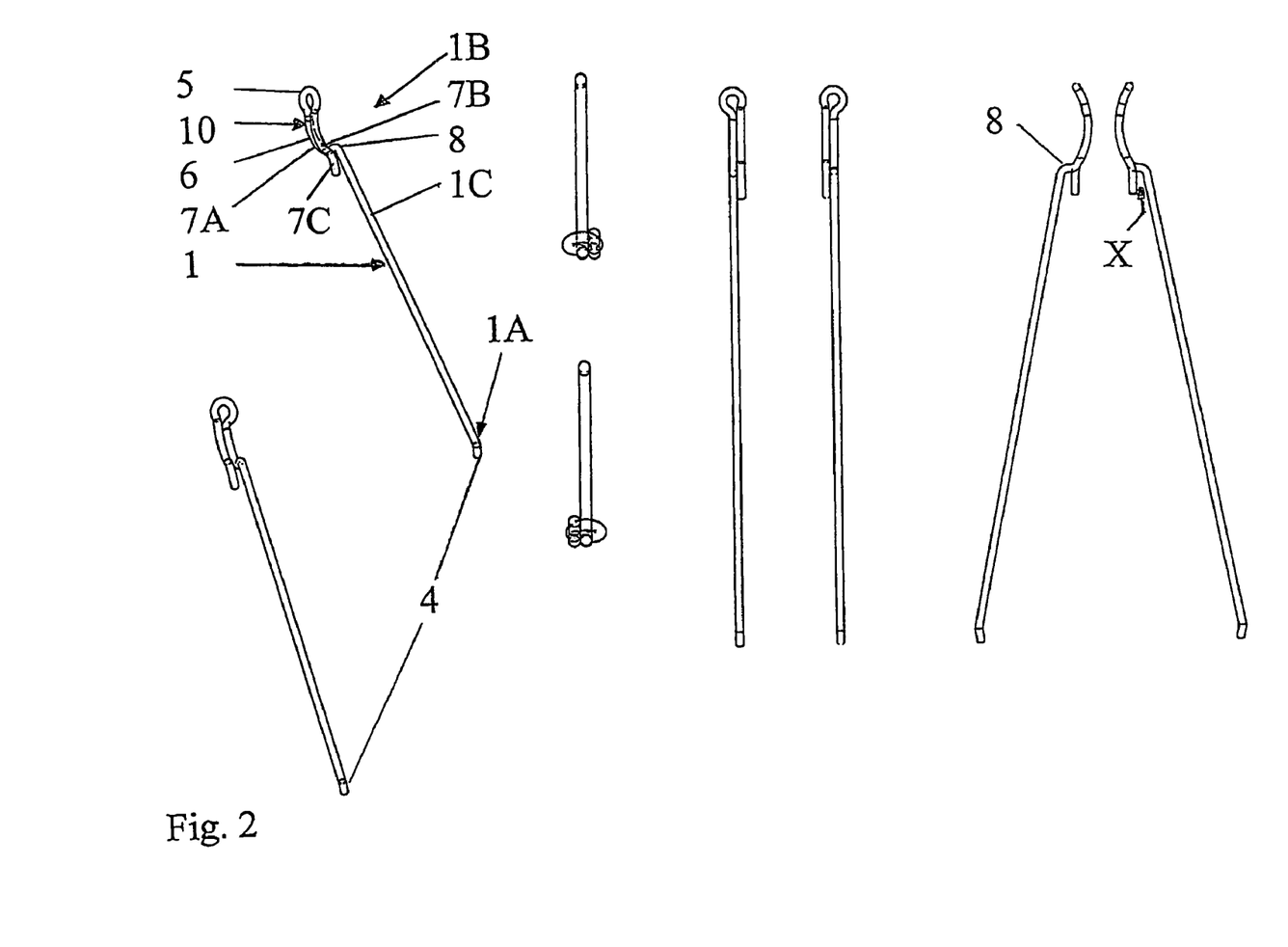
FIG. 2 shows different views of a pin in accordance with a first preferred embodiment of the present invention.
Figure 3:
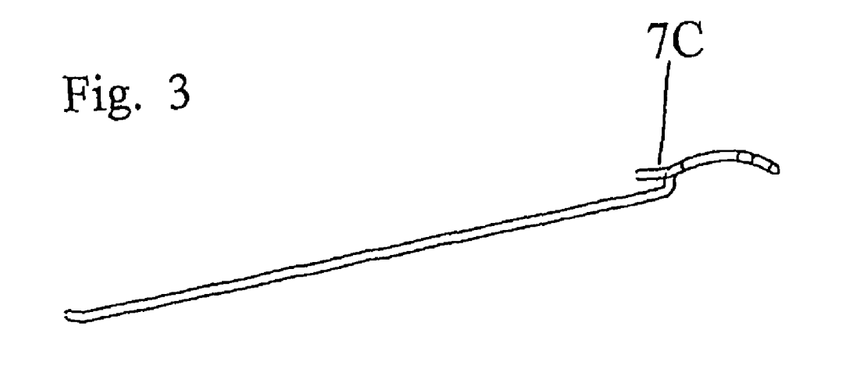
FIGS. 3 and 4 show different plan views of the first pin embodiment.
Figure 4:
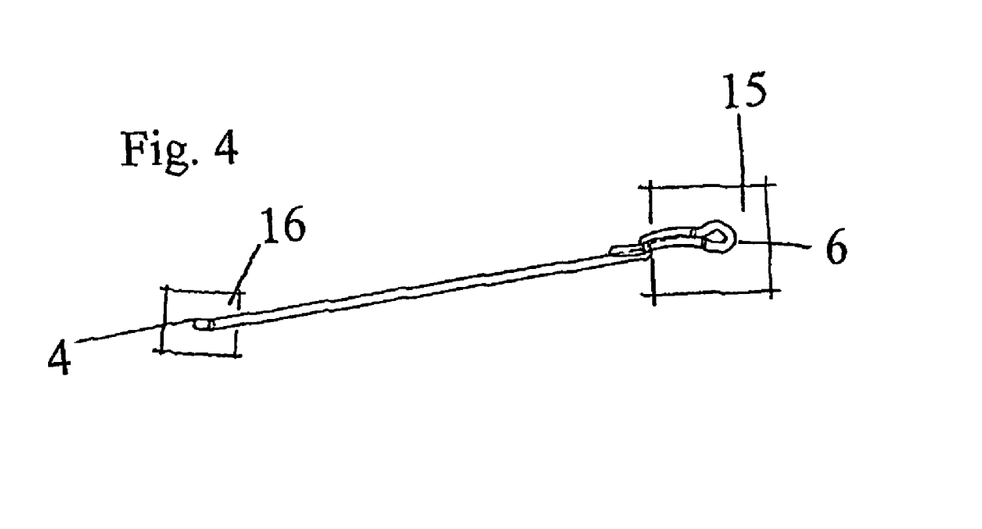
Figure 5:
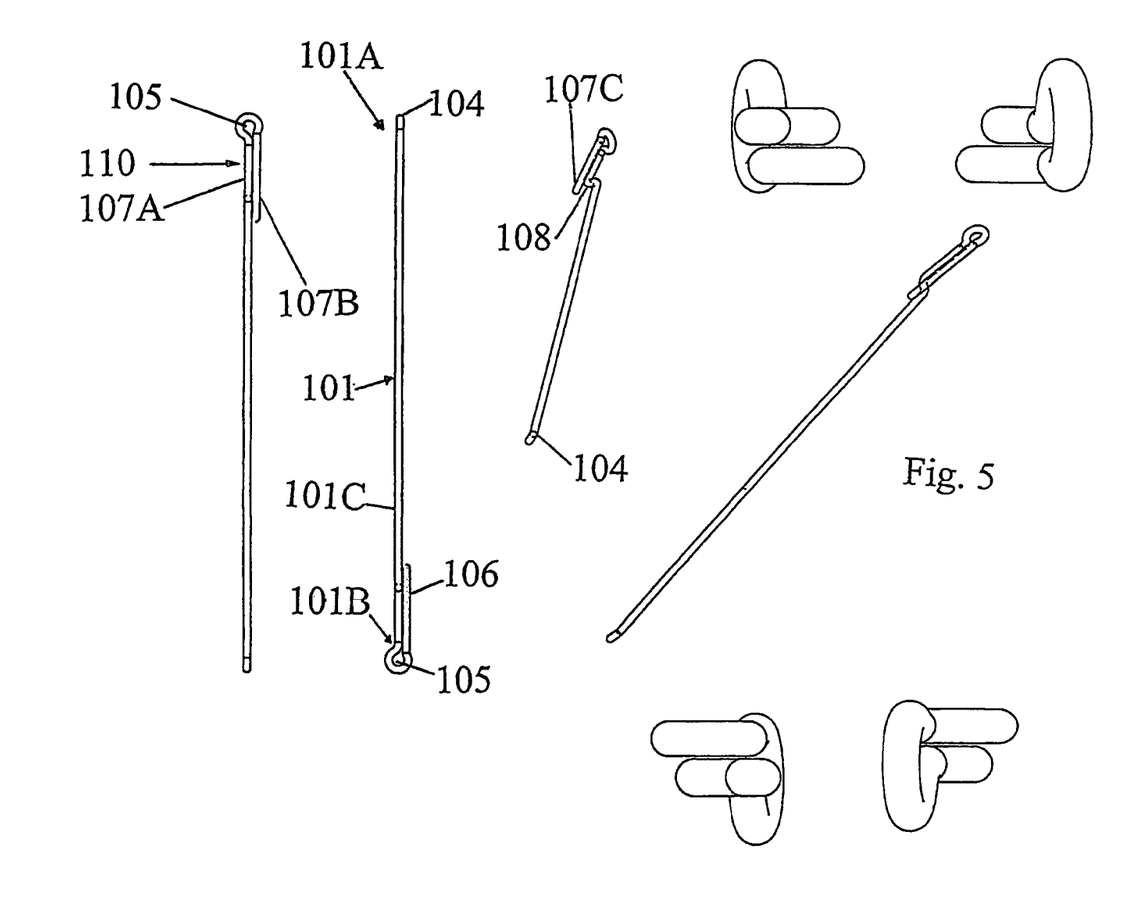
FIG. 5 shows different views of a pin in accordance with a second preferred embodiment of the present invention.
Figure 6:
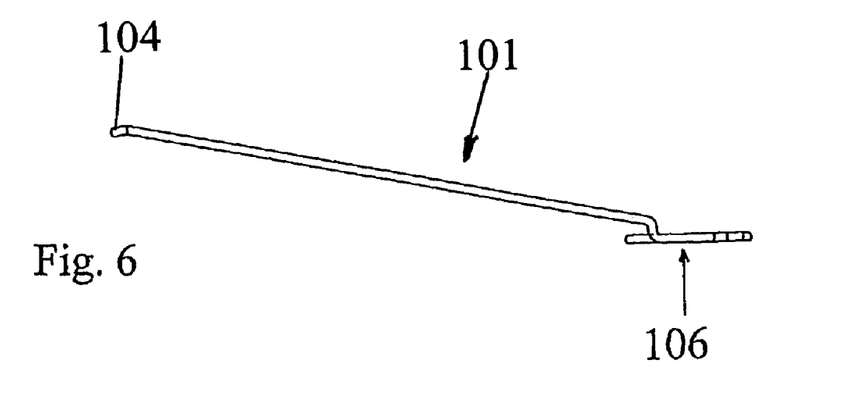
FIGS. 6-10 show different plan views of the second pin embodiment.

Both pin sections 7A, 7B; 107A, 107B; 207A, 207B can be straight (see FIG. 5 and FIG. 14) or curved (see FIG. 2).

Figure 14:
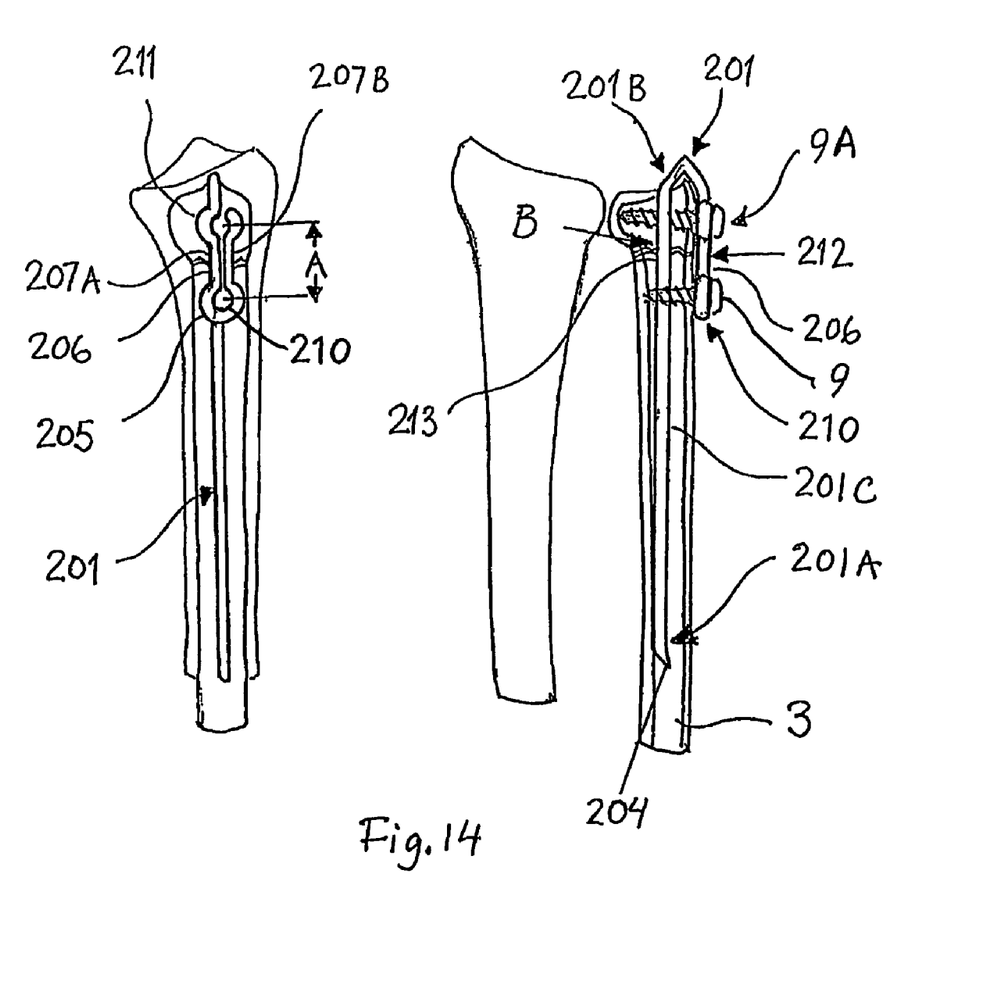

FIG. 14 shows a variant where the pin 201 is bent back at the end 201B through an angle of about 180° and is especially suitable for anchorage with screw 9 to the bone 3 in question.

A hole-shaped outer eye 5; 105; 205, designed to receive therein a fixation screw 9 or some other fixing device, is located adjacent to the pin end sections' outer ends 10; 110; 210, respectively. In that connection, in the FIG. 14 variant a further hole-shaped inner eye 211 can be arranged, which is designed to receive therein a further fixation screw 9A, or some other fixing device, and which is located at a distance A from the first-mentioned outer eye 205.

The rear support part 206 of the pin 201 that includes the above-mentioned screw eyes 205, 211 is bent back at an angle of about 180° so that the reformed section 212 is located parallel with the remaining section 213 of the pin 201 and is kept at the distance B from it, as shown in FIG. 14. On the other pins 1; 101 the above-mentioned blunt angle 8, 108, respectively, is essentially right-angled. The function of the bending back is for the pin to be kept constantly in position at fracture 2, with the pin's transverse section extending across the linear extension of bone 3, and with the pin's both parallel pin sections 207A, 207B arranged to extend internally within and externally on the outer surface of the bone, respectively.

The above-mentioned angled, rounded end sections 4; 104; 204 and the above-mentioned bent sections 6; 106; 206 extend along each plane 15,16 (see FIG. 4), which are essentially arranged at right angles in relation to each other.

The fixation pin is principally of a flat design, with a principally circular cross section, formed from materials such as spring steel, titanium, stainless steel, plastic, resorbing material, or a composite plastic.

Figure 15:
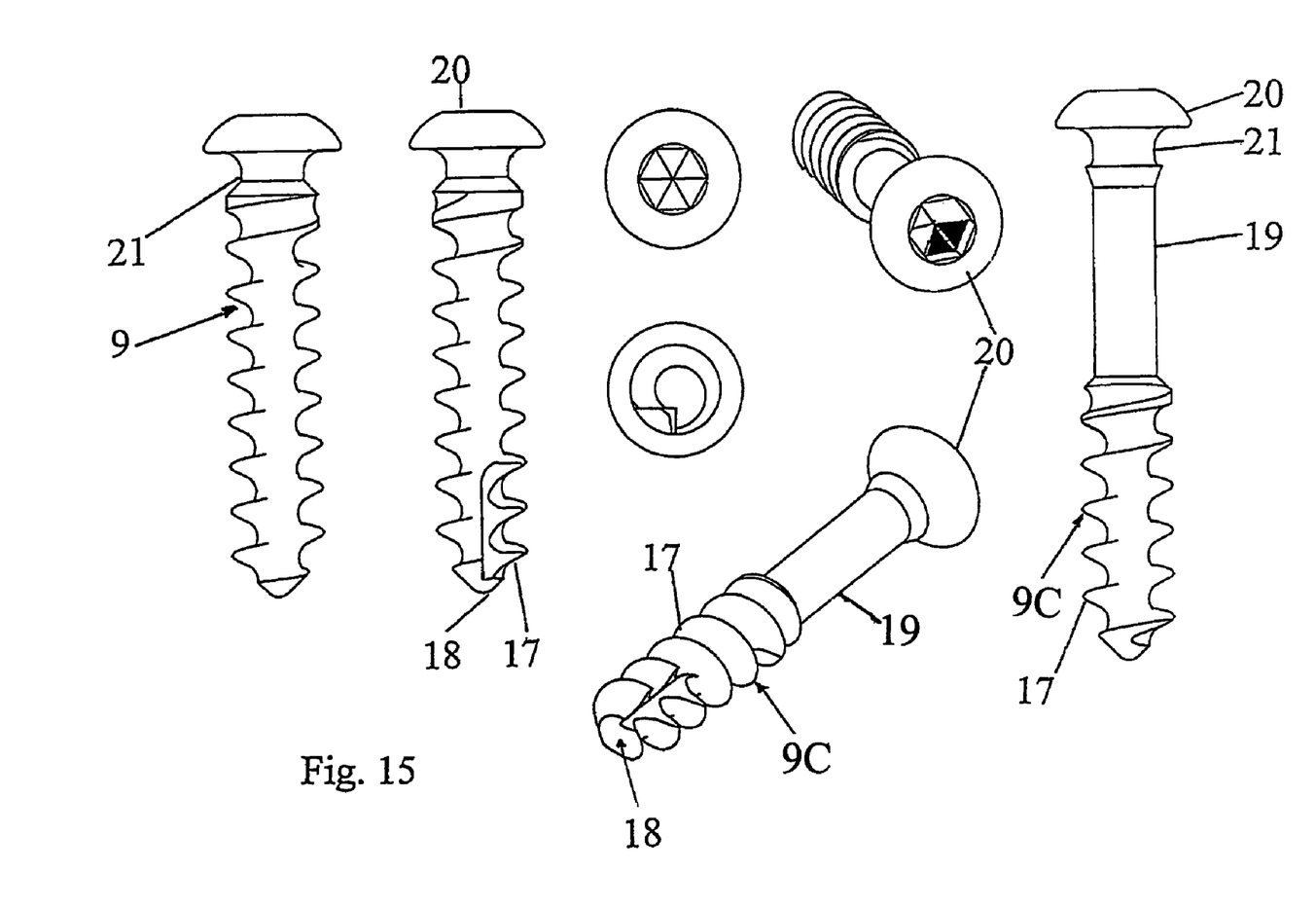
FIG. 15 shows different views of a bone fixation screw in accordance with the invention, and FIG. 16 schematically shows a sketch of how a pin is applied in a bone fracture and thereafter inserted in position.

Screw 9, which is arranged to secure pins 1; 101; 201 in position, is shown in FIG. 15. The screw includes threads 17 from the outer end 18 of the screw up to a plain, unthreaded section 19 that is located next to or at a distance from the screw head 20. A ring-shaped receiving section 21 is thereby arranged on the screw 9 to be able to be surrounded by the ring shaped eyes 5; 105; 205 in the secured position and clicked in position therein. Depending upon the appearance of the bone fracture 2, a screw that is suitable for each type of fracture is used.

A variant of the screw includes threads right up to the screw head 20. The above-mentioned threads are designed to work together with the pin's round cross section part.

Figure 7:
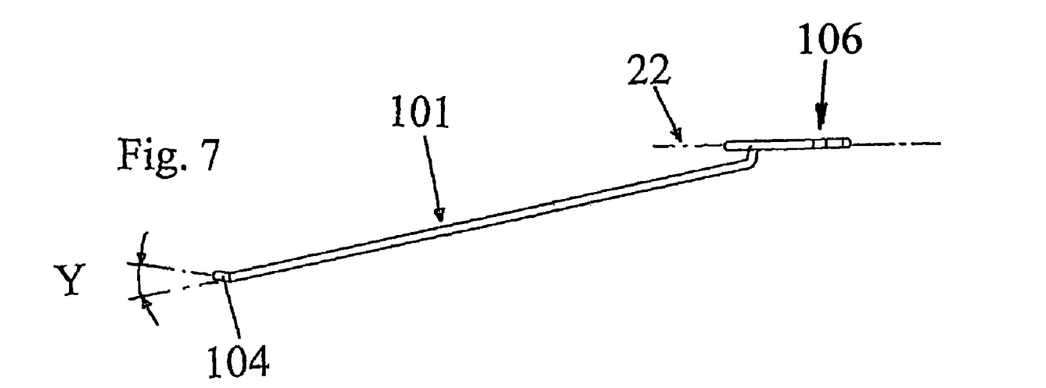
Figure 8:
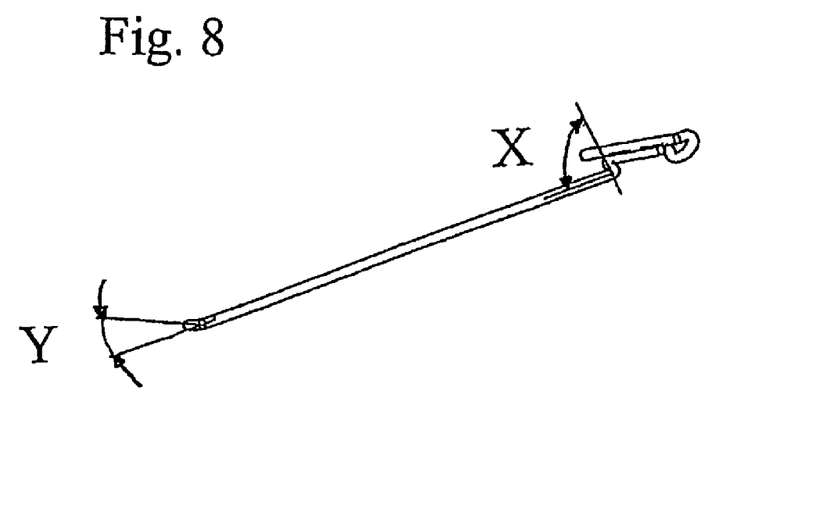
Figure 9:
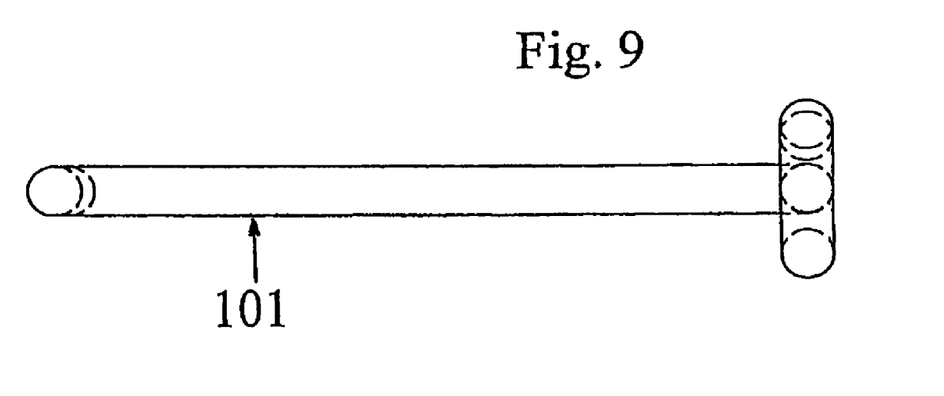
Figure 10:
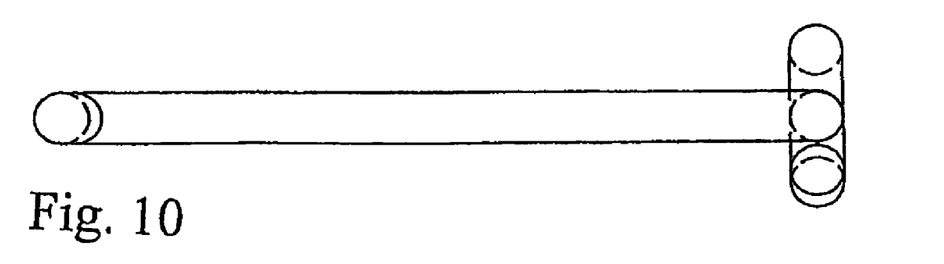
Figure 11:
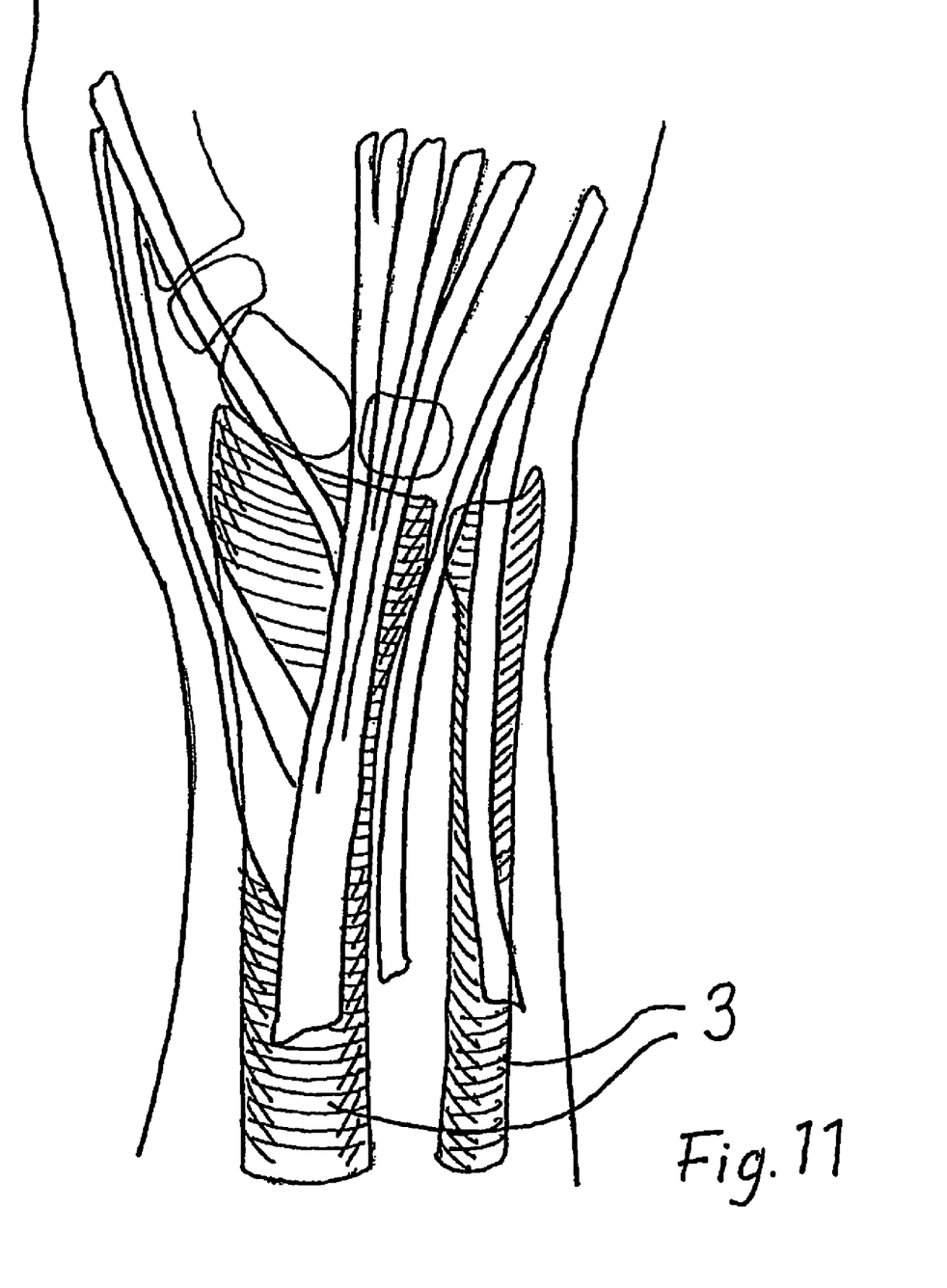
FIGS. 11-14 show different examples of the assembly in a bone of different types of pins in accordance with the present invention.

As shown for example in FIG. 7, angled, rounded front sections 4; 104; 204 of the pins can be inclined at an angle Y between 10°-30° to the pin longitudinal axis and angled relative to the double bent rear support section 106 that lies in common plane 22.

Figure 12A:
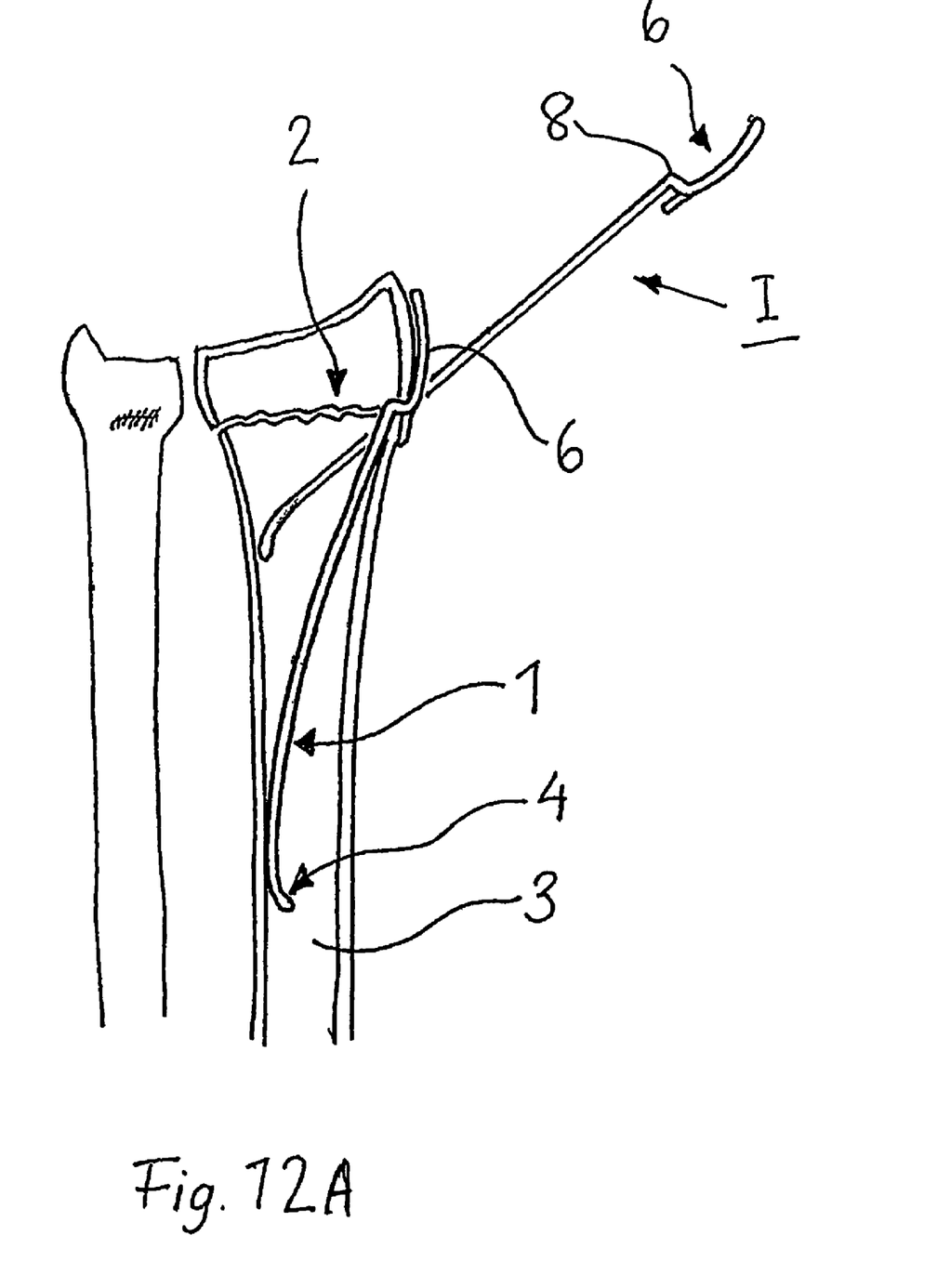
Figure 12B:
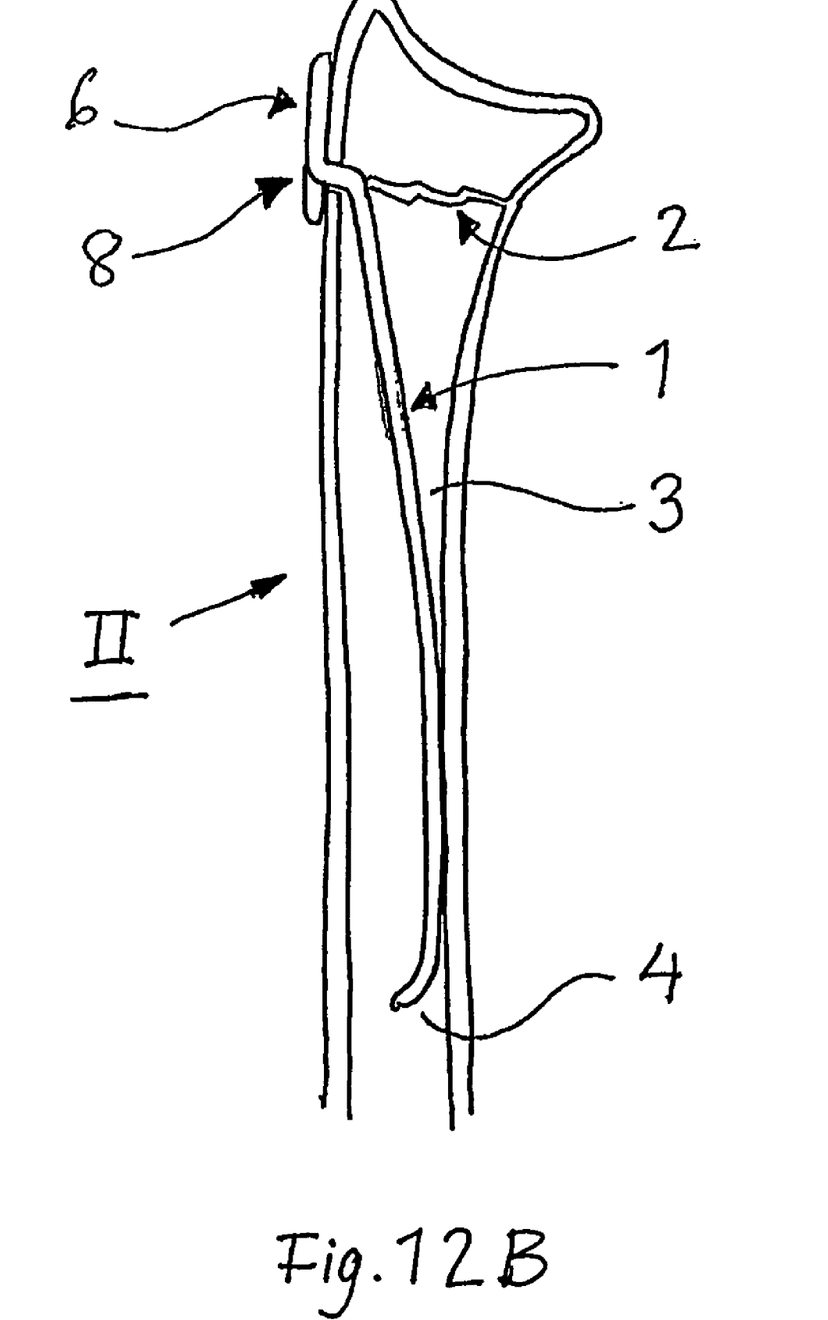
Figure 13:
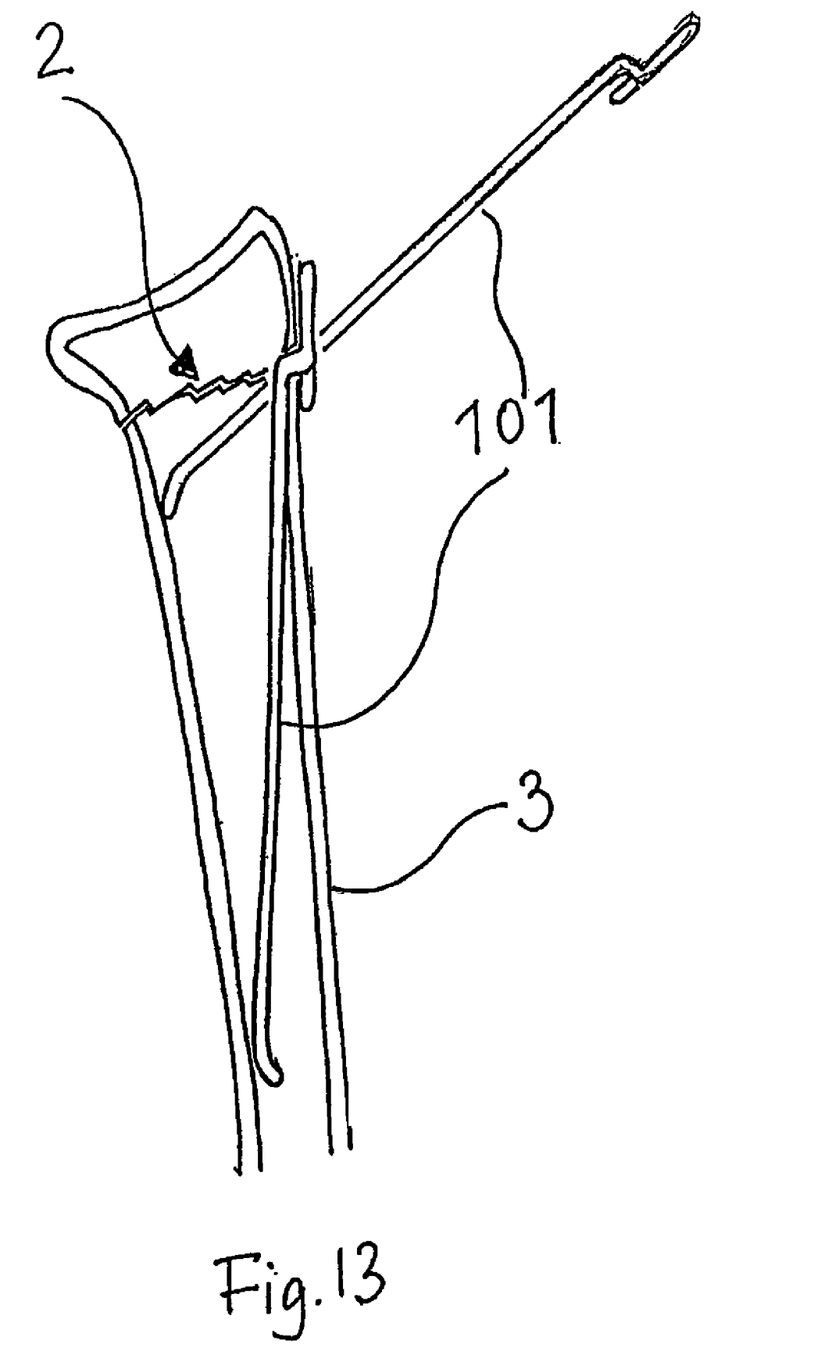

Depending upon the type of fracture on the bone 3 that has occurred at the time of the accident, different pins of the type described above are used, and the application of the same can vary. As shown in FIG. 12A, the pin 1 in accordance with the examples shown in FIGS. 1-4 is a so-called "Radius Contour Pin" 1 and that type of pin is inserted through the actual radial fracture 2, as represented by position I of FIG. 12A. As shown in FIG. 12B, bent rear support section 6 of the pin 1 when it is in position II of FIG. 12B will lie tight against the bone 3 and thereby minimize irritation of nerves and tendons. The extended section, located outside of bone 3, of the rear support section 6 produces good support against the close lying fragment of the bone 3. The possibility of additional fixation with screw 9 also exists. The angled, rounded front part 4 facilitates sliding of the pin against the inside wall of the cortex of bone 3.

The pin in accordance with the example as shown in FIGS. 5-10 is a so-called "Dorsal pin" 101. Such a pin is arranged to be inserted through a "dorsal" fracture line and is arranged to support the bone fragment with the support section 106 located at the rear of the pin 101. The double rear pin sections 107A, 107B on the above-mentioned rear support section 106 distribute the pressure across a large area and reduce the risk of cutting into the patient's brittle bone. The possibility of extra bone fixation with screws also exists with pin 101. The dorsal shank on the pin provides good support to the distal fragment, and the transverse bend back prevents the pin from starting to move. The extra cortical shank, i.e., the section of the pin which is arranged to come outside of the bone cortex on the bone, exists in different lengths in order to be varied depending upon different types of fracture positions. Even with that pin it is possible to anchor it with screws to further increase stability.

Effective contact and support against bone 3 is achieved with the above-mentioned protruding pin end section through the free end 7C; 107C of one pin end section 7B; 107B of both pin end sections 7A, 7B; 107A, 107B that extends past the bent sections 8; 108 of the pins 1; 101.

Figure 16:
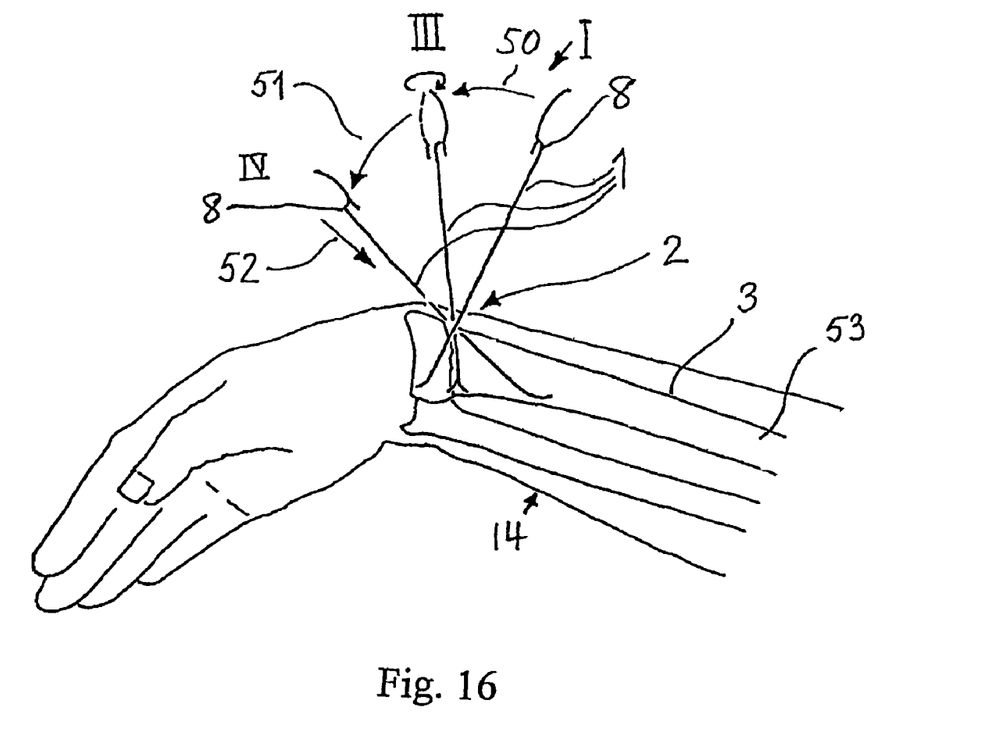

FIG. 16 shows how the pin 1 in position I is first inserted through the fracture site 2 in a forearm 14 across the longitudinal direction of bone 3. After insertion the pin 1 is tilted in the direction of arrow 50 to an intermediate position III at which the pin is rotated about 180°, whereupon continued tilting of pin 1 occurs in the direction of arrow 51 to the final position IV. Pin 1 is then pressed inward with its front section in the direction of arrow 52 internally into the bone-marrow 53 within the bone 3 a distance so that the angled section 8 on the pin 1 extends across at the fracture site 2 and continues with its rear support part 6 to rest against the outside of the bone 3, as shown in FIG. 12B at the final position II. If the fracture is simple, it can be sufficient for one pin to be used, but otherwise two or more pins must be used to effectively hold together the bone sections at the fracture site 2.

Finally, in FIG. 14 examples of a so-called "Ulna Pin" 201 are shown, which is used with extremely complex fractures with many small bone fragments, such as a malpositioned fracture, sometimes with several fragments, on the lower part of the elbow bone. The pin 201 is inserted through the fracture's distal section into the medullary canal of the ulna. It is then secured to the bone 3 with fixation screws 9, 9A which are received in the screw eyes 205, 211 on the back bent reformed section 212 of the pin 201 to hold the bone fragments relative to the part of the bone that has not been fractured. The pin can be left in the bone in the form of an implant.

On account of the pin's spring properties, the pin stabilizes the fragment of the fracture through the tension between the distal cortex and the proximal medullary canal. The pin is inserted until the transverse section of the pin snaps into the fracture at the fracture line.

An additional advantage offered by the present invention is that the pin in accordance with the invention is anatomically designed so that it lies tight against the bone, and thereby effectively increases the contact surface against the contact section of the bone.

Consequently, the pin is ideal to be utilized both to position the fracture into the right position and to hold together the bone fragments.

French published patent application FR 2,728,155 A1 describes a typical so-called intermedullary nail, i.e., a device designed to stabilize a broken tubular bone through insertion in the medullary canal on each side of the fracture. The insertion in the medullary canal takes place through an artificial channel effected into one end in one of the fragments.

The present invention's radial contour pin and dorsal radius pin are inserted into the fracture site through the existing fracture gap. Accordingly, the pin is only inserted into the medullary canal of only one of the fracture fragments, which secures the pin. In turn, the pin provides support to the other fragment by resting against that fragment's outer area.

The bending (7) of the device described in the French publication has as an object to permit the insertion of the medullary nail into the medullary canal via an (artificial) opening in the bone that does not lie in the medullary canal's longitudinal direction.

The present invention's principle of operation involves the external shank to be connected to the existing anatomy/topography of the outside of the distal fragment, which is why the bend connects to the existing anatomy. In addition, the pin in accordance with the present invention is double bent, with a parallel offset of the extramedullary and the intramedullary parts to create an intermediate shank (8, 108, 208) (intrafocal shank) whose length corresponds to the thickness of the cortical bone at the fracture gap.

The device in the French publication has two parallel intramedullary shanks.

The invention has one intramedullary shank, but different forms on the extramedullary shank, which are chosen depending upon how the fracture appears, and where the pin is to be inserted.

On the device disclosed in the French publication the extra cortical curve is the necessary connection between the two intramedullary shanks.

In the present invention, the extra cortical part is designed to give the greatest possible contact against the distal fragment's surface and by doing so to achieve stability in the same plane as the short shank. That has been achieved through the anatomically designed hooks, and thus an even larger contact surface is achieved extra cortically through doubling and by the ring form of the external shank.

The device disclosed in the French publication has been made securable through different fastening devices that can be connected to the extramedullary curve. That has been done to prevent the device from sliding out of the medullary canal, a problem that is known for straight and slightly angled intramedullary nails.

The pin in accordance with the present invention is stabilized in the skeleton through the intra focal shank (8), i.e., the connection shank between the intra and the extramedullary parts of the pin, which is perpendicular to the fracture line and will hook into the fracture line. Further fixation in the proximal fragment is obtained through the extra cortical shank's returning section being so long that it passes the fracture gap and with that runs in parallel to the intramedullary shank on the way from the fracture gap to the extramedullary shank's tip. This produces a "fork" that straddles the cortex of the proximal fragment. The eye in the pin in accordance with the present invention can also be used to fix the distal fragment to the device with a special screw, through which stability of the distal fragment is increased. The screw is thus not intended to prevent the pin from sliding out of the medullary canal.

A pure intramedullary device like that disclosed in the French publication can not safely stabilize a fractured wrist. The device must be partly inserted through the joint surface, or very close to the joint surface, which could injure the wrist.

Further, the contact surface between the device and the distal bone fragment would be so small that stability would be insufficient.

The present invention includes different forms on the extramedullary shank, which are chosen depending upon how the fracture appears and where the pin is to be inserted. In general, at least two pins are used, but sometimes three different pins are used, inserted through separate openings, so that the fracture is stabilized on different planes. The anatomical design of the pin's extra cortical section is a prerequisite for the stabilization of the brittle (osteoporotic) bone, which is usually the cause of fractured wrists in the elderly. The pin's design utilizes the curved form of the cortical bone in the fragment close to the distal joint, so that with a small amount of foreign material a large contact surface is provided, which distributes the pressure from the pin over a greater part of the distal fragment.

The angled front section (3, 4), which is shown in the French publication, is a well-known design solution for all implants that are inserted in the medullary canal. That hook can be said to make up a "ski tip," which allows the implant to slide down despite the fact that the implant is held angled to the medullary canal's longitudinal axis. The top of that "ski tip" is sharp in order to able to penetrate the cortex during insertion.

The pin in accordance with the present invention has a top with a more rounded design in order to allow maneuvering inside the medullary canal via the fracture gap, without catching against the opposite side of the medullary canal or penetrating the opposite cortex. That characteristic is only utilized at the start of the insertion. Further inside the medullary canal the pin can be rotated when the bend close to the rounded tip is utilized to coax the pin past any unevenness in the medullary canal. That step is impossible with the pin disclosed in the French publication, because due to its design it can not be rotated.

In summary the above shows that, the device disclosed in the French publication and the pin in accordance with the present invention have different designs, different functions, and different areas of application.

There is therefore no motivation for one skilled in the art to invent the structural design in accordance with the present invention.

The present invention is naturally not limited to the above description or to the designs shown in the appended drawings. Modifications are possible, especially with regard to the character of the different parts, or through the use of equivalent technology, without deviating from the restricted area for the invention, such as it is defined in the claims.

What is claimed is:

1. A surgical fixation pin of flexible material for use in fractures in bones in arms or other body parts to provide support of a bone while the fracture heals, said pin comprising:
   an elongated body member having opposite ends,
   wherein a first, front intramedullary end section includes a unitary, angled front section, and at a second, rear extramedullary end section the pin has a double bent extracortical support section provided with an anchor eye in the form of a ring-shaped outer eye for receiving therein a first fixation screw, wherein the ring-shaped outer eye is located adjacent an outermost end of the second extramedullary end section of the pin,
   wherein the intramedullary end section and the extramedullary end section are substantially parallel in relation to each other,
   wherein both the angled front end section and the rear end section of the pin each extend within respective separate planes that are substantially perpendicular in relation to each other,
   wherein a center section of the pin is formed by an intermediate section that includes at the extramedullary end section of the center section of the pin an extension in the form of a shank that is substantially perpendicular relative to the intermediate section and to the double bent extracortical extramedullary section,
   wherein the double bent extracortical support extramedullary section is formed from an end section of the pin extending from the intermediate section and has two rear pin end sections lying adjacent to each other,
   wherein the front section is angled between 10°-30° relative to the elongated body member,
   wherein the front section is angularly positioned relative to a common plane defined bar double bent extracortical support section, and
   wherein the fixation pin is formed from wire.

2. A surgical fixation pin in accordance with claim 1, wherein both pin end sections are, straight.

3. A surgical fixation pin in accordance with claim 1, wherein both pin end sections are curved.

4. A surgical fixation pin in accordance with claim 1, including an additional, inner eye for receiving a second fixation screw therein, wherein the additional inner eye is spaced inwardly from the outer eye.

5. A surgical fixation pin in accordance with claim 1, wherein the pin is formed as a flat spring steel element.

6. A surgical fixation pin in accordance with claim 1, wherein a free end of the second end section extends past the shank of the pin.

7. A surgical fixation pin in accordance with claim 5, including a fixation screw for affixing the pin to a bone, wherein the screw includes threads up to an unthreaded section adjacent to a head of the fixation screw, and wherein a ring-shaped receiving section is enclosed by the ring shaped outer eye.

8. A surgical fixation pin in accordance with claim 1, including a fixation screw having threads that extend to a head of the fixation screw, and wherein threads of the fixation screw engage with the ring-shaped outer eye.

9. A surgical fixation pin in accordance with claim 1, wherein the wire has a dimension of about 1.6 mm.

10. A surgical fixation pin in accordance with claim 1, wherein the wire has a circular cross section.

* * * * *